United States Patent [19]

Tuneburg

[11] Patent Number: 5,575,644
[45] Date of Patent: Nov. 19, 1996

[54] ORTHODONTIC APPLIANCE

[75] Inventor: Lee H. Tuneburg, Sheboygan, Wis.

[73] Assignee: American Orthodontics, Sheboygan, Wis.

[21] Appl. No.: 294,369

[22] Filed: Aug. 23, 1994

Related U.S. Application Data

[63] Continuation-in-part of Ser. No. 29,762, Mar. 11, 1993, abandoned.

[51] Int. Cl.$^6$ .................................................. A61C 3/00
[52] U.S. Cl. ............................................................ 433/8
[58] Field of Search ................................ 433/8, 9, 10, 11, 433/12, 13, 14, 15, 16, 17, 18, 19, 20, 21, 22, 23

[56] References Cited

U.S. PATENT DOCUMENTS

| | | | |
|---|---|---|---|
| 2,176,837 | 10/1939 | Ellis . | |
| 3,765,091 | 10/1973 | Northcutt | 32/14 A |
| 3,922,787 | 12/1975 | Fischer | 32/14 A |
| 3,930,311 | 1/1976 | Andrews | 32/14 A |
| 4,050,156 | 9/1977 | Chasanoff | 32/2 |
| 4,052,792 | 9/1977 | Biederman | 32/14 A |
| 4,107,844 | 8/1978 | Kurz | 32/14 A |
| 4,216,583 | 8/1980 | Reynolds | 433/9 |
| 4,219,617 | 8/1980 | Wallshein | 433/8 |
| 4,299,569 | 11/1981 | Frantz | 433/8 |
| 4,302,532 | 11/1981 | Wallshein | 433/8 |
| 4,322,206 | 3/1982 | Reynolds | 433/9 |
| 4,470,809 | 9/1984 | Klepacki | 433/15 |
| 4,559,013 | 12/1985 | Amstutz et al. | 433/22 |
| 4,639,218 | 1/1987 | Jones et al. | 433/8 |
| 4,681,538 | 7/1987 | Deluca et al. | 433/9 |
| 4,717,341 | 1/1988 | Goldberg et al. | 433/23 X |
| 4,731,019 | 3/1988 | Martin | 433/166 X |
| 4,784,606 | 11/1988 | Jones et al. | 433/8 |
| 4,902,224 | 2/1990 | Collins et al. | 433/8 |
| 4,915,625 | 4/1990 | Tsukuma et al. | 433/8 |
| 4,932,865 | 6/1990 | Collins et al. | 433/8 |
| 4,954,080 | 9/1990 | Kelley et al. | 433/8 |
| 5,032,080 | 7/1991 | Hakansson | 433/8 |
| 5,066,225 | 11/1991 | Forbes Jones | 433/8 |
| 5,078,596 | 1/1992 | Carberry et al. | 433/8 |
| 5,104,591 | 4/1992 | Maushara et al. | 264/16 |
| 5,124,179 | 6/1992 | Garg et al. | 427/249 |
| 5,126,206 | 6/1992 | Garg et al. | 428/408 |
| 5,135,808 | 8/1992 | Kimock et al. | 428/336 |
| 5,147,687 | 9/1992 | Garg et al. | 427/249 |
| 5,160,544 | 11/1992 | Garg et al. | 118/724 |
| 5,186,973 | 2/1993 | Garg et al. | 427/590 |
| 5,190,807 | 3/1993 | Kimock et al. | 428/216 |
| 5,203,804 | 4/1993 | Nikutowski et al. | 433/23 X |
| 5,256,447 | 10/1993 | Oxman et al. | 427/207.1 |

OTHER PUBLICATIONS

Improved Hardness and Wear Properties of B-ion Implanted Polycarbonate; Journal of Material Research; vol. 7, No. 7, Jul. 1992 pp. 1900–1911.

Primary Examiner—Nicholas D. Lucchesi
Attorney, Agent, or Firm—Godfrey & Kahn, S.C.

[57] ABSTRACT

An improved orthodontic appliance is described which includes a main body manufactured from a polymeric material. A polycrystalline diamond coating is deposited on the main body. The coating has a thickness greater than 0.5 microns and is substantially transparent to the visible light spectrum and is deposited at a temperature of less than 140° C.

23 Claims, No Drawings

5,575,644

ORTHODONTIC APPLIANCE

This is a continuation-in-part of application Ser. No. 08/029,762 filed on Mar. 11, 1993, now abandoned.

BACKGROUND OF THE INVENTION

The present application is a continuation-in-part of application Ser. No. 08/029,762 and which was filed on Mar. 11, 1993, now abandoned.

1. Field of the Invention

The present invention relates to an improved orthodontic appliance, and more particularly, to a composition which may be applied to the orthodontic appliance thereby increasing the strength of same, and, simultaneously providing a durable and substantially transparent finish or coating which imparts improved aesthetic and other performance characteristics to the orthodontic appliance.

2. Description of the Prior Art

The prior art is replete with numerous examples of improved orthodontic appliances which have been utilized by clinicians in the treatment of various orthodontic maladies. As a general matter, manufacturers of orthodontic appliances have endeavored through the years to produce aesthetically pleasing appliances, but their efforts have met with only limited success. For example, and while many of the orthodontic products which have been introduced have had varying degrees of success, they have each had shortcomings which have detracted from their usefulness. These deficiencies in the prior art devices have often manifested themselves in increased amounts of clinician's time, or otherwise resulted in broken or damaged appliances, and on some occasions, patient trauma.

Examples of various orthodontic appliances which have been introduced to address various aesthetic considerations have included so-called "pure" polycarbonate brackets. While the aesthetic considerations of these types of brackets were generally quite improved, in relative comparison to metal brackets, for example, they have not been as successful as manufacturers once hoped. In particular, pure polycarbonate brackets are difficult to adhesively bond to a patients teeth and have, from time to time, detached or debonded from the patients teeth due to occlusal or masticatory forces. Additionally, such brackets or appliances are somewhat weak thereby causing the appliances to fail or otherwise distort over time. Moreover, these same brackets or appliances are sometimes chemically reactive with the fluids found in the patients' oral cavity and therefore may tend to stain or otherwise discolor over time.

In contrast to the "pure" polycarbonate brackets noted in the paragraph above, glass-filled polycarbonate is much stronger, relatively speaking, than pure polycarbonate. However, this material suffers from the same problems as pure polycarbonate with respect to bonding and staining. However, glass-filled polycarbonate has excellent aesthetic qualities inasmuch as that it normally blends in quite well with the natural tooth structure.

Other materials have been employed in the manufacture of orthodontic appliances such as LCP, polyetherimide, PET, PES, and PS, however, these materials have been less than ideal due to a lack of strength or bonding difficulties. Furthermore, these same materials are not translucent or are colored and therefore, their aesthetic value is considered somewhat marginal.

Other materials which have been utilized in combination with glass-filled polycarbonates have included assorted metals. For example, orthodontic appliances have been manufactured which have included a stainless steel insert. While these devices have operated with some degree of success, they have not been well received from an aesthetic view point because the gray color of the metal may often be seen through the bracket. Also, the same orthodontic appliances have exhibited tie wing strength problems and also some propensity for failure as when the metal slots are pulled out of the bracket. These brackets are similarly difficult to bond in view of the presence of the polycarbonate.

Another material utilized in the manufacture of orthodontic appliances is polycrystalline $\alpha$-alumina. Polycrystalline $\alpha$-alumina is generally considered to have excellent aesthetic characteristics, that is, it blends in well with a patients natural tooth structure, however, orthodontic appliances manufactured with such materials have been less than satisfactory due to their propensity to fracture, especially in the tie-wing or arch slot areas. Additionally, appliances utilizing this same material, while acceptable from an aesthetic standpoint are relatively costly to produce, and have exhibited other detrimental performance characteristics such as increased friction in the arch slot areas of a bracket. Many of the same problems related to polycrystalline $\alpha$-alumina are present when utilizing single crystal $\alpha$-alumina. However, when single crystal $\alpha$-alumina is employed in the manufacture of brackets, upon failure, the bracket tends to shatter, as opposed to fracturing.

Other attempts in the art to address these same aesthetic considerations have included the application of polymer or electrostatic pigment coatings on orthodontic appliances. These coatings have been less than satisfactory, however, in view of problems attendant to slot tolerances. Additionally, these coatings have a propensity for chipping off. Furthermore, these coatings are non-translucent and, if the associated bracket is one which includes a metal slot, then, in that event, the gray colored metal may be seen, on occasion, underneath the coating once the coating has chipped off, or otherwise worn away. Finally, ceramic materials have been widely used for orthodontic appliances. However, these materials have many disadvantages including difficulties in bonding, and extreme brittleness under some conditions. Furthermore, such brackets potentially can abrade the enamel of a patients teeth and normally must be made larger than a corresponding metal bracket for similar strength.

Therefore, it has long been known that it would be desirable to have an improved orthodontic bracket which has acceptable aesthetic qualities, and which further avoids the shortcomings attendant with the prior art materials and practices.

SUMMARY OF THE INVENTION

Therefore, it is an object of the present invention to provide an improved orthodontic appliance.

Another object of the present invention is to provide an improved orthodontic appliance which is manufactured from a glass-filled polycarbonate and which further has a coating applied thereto which improves the strength of the polycarbonate, and is translucent, thereby causing the orthodontic bracket to become substantially unnoticeable when bonded on a patient's tooth.

Another object of the present invention is to provide an improved orthodontic appliance which has an amorphous diamond coating applied thereto, and wherein the same coating is greater than 0.5 microns in thickness.

Another object of the present invention is to provide an improved orthodontic appliance which has a polysiloxane coating applied thereto, and wherein the same coating has a thickness of about 2 to 5 microns.

Another object of the present invention is to provide an improved orthodontic appliance which has applied thereto a coating of polysiloxane which has a thickness of about 2 to 5 microns, and an amorphous diamond coating which has a thickness dimension of preferably 1 to 8 microns.

Another object of the present invention is to provide an improved orthodontic appliance which has a coating applied thereto which increases the strength of the orthodontic appliance; which has an enhanced coefficient of friction; and which further is chemically resistant to degradation.

Another object of the present invention is to provide an improved orthodontic appliance which has improved optical clarity and which further resists arch wire torquing forces and tie-wing metal ligature destruction.

Another object of the present invention is to provide an improved orthodontic appliance which is characterized by ease and simplicity in its utilization, and which further can be manufactured at a substantially nominal price in relative comparison to the prior art devices.

Further objects and advantages are to provide improved elements and arrangements thereof in an orthodontic appliance for the purposes intended, and which is dependable, economical, durable, and fully effective in accomplishing its intended purposes.

These and other objects and advantages are achieved in an improved orthodontic appliance of the present invention and which includes an orthodontic appliance having a main body, and an amorphous diamond coating deposited on the main body, the coating imparting increased strength to the main body.

DESCRIPTION OF THE PREFERRED EMBODIMENT

First Form

As noted above, the present invention includes an orthodontic appliance which is manufactured from a material such as glass-filled polycarbonate. Commercially available orthodontic appliances of this description may be secured from American Orthodontics of Sheboygan, Wis. under the "Silkon" trademark. These particular appliances are 20–30% glass-filled polycarbonate. The orthodontic appliances discussed above have a main body which has applied thereto an amorphous diamond coating which has a surface depth of greater than 0.5 microns but which preferably have a thickness of approximately 1 to 8 microns. The amorphous diamond coating is applied thereto by utilizing a vacuum chamber with a Kaufman type ion source.

As should be understood, other objects of interest have been coated utilizing the same or similar techniques with amorphous and polycrystalline diamond films. Such articles of manufacture and techniques are disclosed in further detail in U.S. Pat. Nos. 5,124,179; 5,126,206; 5,135,808; 5,147,687; 5,160,544; 5,186,973; and 5,190,807, all of which are incorporated by reference herein. Additionally, these same orthodontic appliances may be improved as to hardness and wear properties by exposing an orthodontic appliance to Boron ion beam treatments. This technique is disclosed in the reference authored by E. H. Lee et al.; "Improved Hardness and wear properties of B-ion implanted polycarbonate"; Journal of Material Research Vol. 7, No. 7, July 1992. The substance of this article is incorporated by reference herein.

The invention is further illustrated by way of the example which is set forth below:

EXAMPLE 1

A 20–30% glass filled polycarbonate bracket such as that which is sold under the "Silkon" trademark by American Orthodontics of Sheboygan, Wis. was first cleaned, ultrasonically, with methanol and freon. The bracket was then placed in a fixture which was operable to mask the bottom portion of the bracket (that portion which will be adhesively fixed to the patients tooth). The masking is intended to prevent ion deposition on the bottom portion of the bracket. This same fixture is then placed in a vacuum chamber with a Kaufman-type ion source. Following placement of the fixture in the vacuum chamber, argon and methane gases are introduced to the chamber where they are passed over a plurality of electrically charged grids and which strips electrons from the respective gases, thereby ionizing them. These same ions are then accelerated by means of the vacuum, toward the masked orthodontic bracket which is secured in the fixture. This process is undertaken at temperatures of less than 140° C. In this process, carbon and hydrogen ions combine together on the exterior surface of the glass-filled polycarbonate bracket thereby forming an amorphous diamond deposit which has a thickness of greater than 0.5 microns; is transparent to visible light; and which has a coefficient of friction of less than about 0.1. Following application of the amorphous diamond deposit or coating, the orthodontic bracket was inspected and the coating appeared to exhibit excellent adhesion to the orthodontic appliance surface. The coating further appeared to be flexible and very dense. Optical transmission was excellent and the coefficient of friction was within the stated range noted above.

To determine the hardness of the coating, an orthodontic appliance was prepared utilizing the technique noted above, and which had an amorphous diamond coating with a thickness of approximately 3 microns. This bracket was then compared and contrasted with a standard or untreated glass-filled polycarbonate bracket purchased from American Orthodontics of Sheboygan, Wis. under the "Silkon" trademark. By utilizing a standard hardness test, it was determined that the untreated bracket had a hardness value of approximately 16.9 plus or minus 2.1 MHV when exposed to a 50 gram load. However, and in contrast, a measurable indentation could not be obtained even when loads exceeding 500 grams were utilized when the treated bracket was tested. At these increased loads, the uncoated base portion of the treated brackets deflected rendering any further measurements meaningless.

EXAMPLE 2

To determine the coefficient of friction exhibited by the brackets of the present invention, the following test was utilized. Brackets, manufactured in accordance with the present invention were affixed to a ⅜" diameter steel rod using a cyanoacrylate adhesive. These brackets had a 0.022" slot; 10° positive angulation; and 0° torque. Thereafter, wires were ligated into the bracket slots using 0.045" inside diameter plastic ligatures which are standard in the orthodontic industry. The wire which was ligated into the bracket slot was 1 cm length of 0.021" by 0.025" stainless steel. This wire was subsequently pulled through the brackets at a crosshead speed of approximately 6.35 millimeters per minute with continuous measurement of force applied.

The static and dynamic (kinetic) friction was measured thereafter. In this regard, the static friction measurement simulated the start of tooth movement along an arch wire under applied force, and the dynamic, or kinetic, friction measurement simulated the lowest force required to maintain the movement of the tooth along an arch wire. Following the test, it was determined that with respect to the untreated glass-filled polycarbonate bracket, the static friction was approximately 560 grams and the dynamic friction was approximately 477 grams. However, and when compared and contrasted with the brackets of the present invention, the static friction was approximately 386 grams and the dynamic friction was approximately 361 grams. It is clear, therefore, that the brackets of the present invention have improved coefficients of friction in comparison to untreated glass-filled polycarbonate brackets.

Second Form

The second form of the invention also utilizes a 20–30% glass-filled polycarbonate orthodontic appliance as described above. The main body of the orthodontic appliances has applied thereto a silica monomer composition such as polysiloxane which preferably has a surface depth of between 2 to 5 microns. A suitable polysiloxane composition may be purchased from the Dow Corning Chemical Company, although a number of alternative polysiloxane compositions may be purchased from other suppliers. The polysiloxane coating may be applied in several ways, including spray, spin and dip-coating. The polysiloxane coating is cured by preferably using a UV radiation source which produces radiation at a wavelength of between 200 to 350 nanometers, although curing may also be achieved by heating. Utilizing the test methods outlined above, it has been determined that this coating imparts an increased torque and deformation resistance to the appliance of approximately 33%, and is also extremely tenacious. The resulting polysiloxane layer is also translucent and transparent.

Third Form

The third form of the invention also utilizes a 20–30% glass-filled polycarbonate orthodontic appliance as described above. In this form of the invention the main body of the orthodontic appliances has applied thereto a polysiloxane coating as described above, and which preferably has a surface thickness of between 2 to 5 microns. As earlier described, the polysiloxane coating may be applied in several ways, including spray, spin and dip-coating. The polysiloxane coating is cured by preferably using a UV radiation source at wavelengths of between 200 to 350 nanometers, although curing may also be achieved by utilizing heat. Next, a coating of amorphous diamond is applied over the polysiloxane coating. This amorphous diamond coating has a surface thickness of greater than 0.5 microns but which preferably has a thickness of approximately 1 to 8 microns. The amorphous diamond coating is applied thereto by utilizing a vacuum chamber with a Kaufman type ion source. Utilizing the test methods noted above it has been determined that the coating of the present form of the invention provides further advantages over the previous two forms in view of the propensity for polysiloxane to adhere exceptionally well to the polycarbonate and further provides an improved surface to which the amorphous diamond coating may adhere. In particular, while the first form of the invention improves the strength of a polycarbonate bracket, there is an upper thickness limit which cannot be exceeded. If this thickness limit is exceeded, the optical characteristics of the coating change with the result that the bracket appears darker than the surrounding tooth. This is unacceptable from an aesthetic viewpoint. As a consequence, the third form of the invention provides improved strength relative to the two previously disclosed forms of the invention while simultaneously providing a bracket which is aesthetically appealing.

The various forms of the invention displayed no propensity to degrade when exposed to the fluid present in the oral cavity. Therefore, it is the case that the improved orthodontic appliance of the present invention provides a fully dependable and practical means by which a clinician may treat orthodontic maladies in an acceptable, aesthetically pleasing manner while simultaneously avoiding many of the detriments associated with the prior art devices, and practices. In addition to the foregoing, the improved orthodontic bracket of the present invention shows surprisingly and unusually desirable manufacturing advantages when compared with the prior art, and further displays improved performance characteristics.

It will be apparent to those skilled in the art that the foregoing examples have been made for purposes of illustration and that variations may be made in proportions, procedures, and material without departing from the scope of the present invention. Therefore, it is intended that this invention not be limited except by the claims which follow.

Having described my new invention, what I claim as new and desire to secure by Letters Patent of the United States is:

1. An orthodontic appliance comprising:

a main body;

a layer of polysiloxane on the main body; and a diamond coating deposited over the layer of polysiloxane.

2. An orthodontic appliance as claimed in claim 1, and wherein the diamond coating has a thickness greater than 0.5 microns and is substantially transparent to visible light.

3. An orthodontic appliance as claimed in claim 1, and wherein the layer of polysiloxane has a thickness of greater than 2 microns and is substantially transparent to visible light.

4. An orthodontic appliance as claimed in claim 1, and wherein the diamond coating exhibits a coefficient of friction of about 0.1.

5. An orthodontic appliance as claimed in claim 1, and wherein the diamond coating is applied at a temperature of less than about 140° C.

6. An orthodontic appliance comprising:

a main body; and a polysiloxane coating deposited on the main body, and wherein the polysiloxane coating has a thickness greater than 2 microns and is substantially transparent to visible light.

7. An orthodontic appliance comprising:

a main body manufactured from a material having a predetermined hardness;

a layer of polysiloxane deposited on the main body; and a diamond coating deposited over the layer of polysiloxane.

8. An orthodontic appliance as claimed in claim 7, and wherein the diamond coating is transparent or translucent to visible light, has a thickness greater than about 0.5 microns, and is chemically resistant to degradation occasioned by exposure of the coating to the oral cavity of humans.

9. An orthodontic appliance as claimed in claim 7, and wherein the polysiloxane coating is transparent or translucent to visible light, has a thickness greater than about 2 microns, and is chemically resistant to degradation occasioned by exposure of the coating to the oral cavity of humans.

10. An orthodontic appliance as claimed in claim 7, and wherein the diamond coating has a coefficient of friction of about 0.1, and is further applied at a temperature of less than 140° C.

11. An orthodontic appliance comprising:
   a main body manufactured from a material having a predetermined hardness; and
   a coating deposited on the main body
   and wherein the main body is polycarbonate and the coating is a polysiloxane deposit.

12. An orthodontic appliance as claimed in claim 11, and wherein the coating includes a layer of diamond deposited over the polysiloxane deposit.

13. An orthodontic appliance comprising:
   a main body manufactured from a polymeric material; and
   a polycrystalline diamond coating deposited on the main body and having a thickness greater than 0.5 microns, and which is substantially transparent to visible light, the coating deposited at a temperature of less than about 140° C.

14. An orthodontic appliance comprising:
   a main body manufactured from a polymeric material; and
   a polysiloxane coating deposited on the main body and having a thickness greater than 2 microns, and which is substantially transparent to visible light.

15. An orthodontic appliance comprising:
   a main body manufactured from a polymeric material;
   a first layer of polysiloxane deposited on the main body and having a thickness dimension of greater than 2 microns;
   and a second layer of polycrystalline diamond deposited on the polysiloxane layer and having a thickness dimension of greater than 0.5 microns, the polycrystalline diamond coating deposited at a temperature of less than 140° C.; and wherein the first and second layers are substantially transparent to visible light.

16. An orthodontic appliance comprising:
   a main body manufactured from a polymeric material; and
   a diamond coating deposited on the main body, the coating imparting increased strength to the main body.

17. An orthodontic device as claimed in claim 16, and wherein the diamond coating is an amorphous diamond coating.

18. An orthodontic device as claimed in claim 17, further comprising a polycrystalline diamond coating on top of the amorphous diamond coating.

19. An orthodontic device as claimed in claim 16, and wherein the diamond coating is a polycrystalline diamond coating.

20. An orthodontic appliance comprising:
   a main body manufactured from a polymeric material;
   a first layer of material deposited on the main body, strongly adhering thereto, and providing a surface to which a diamond coating adheres; and
   a second layer of material deposited on the first layer of material, the second layer of material imparting increased strength to the main body,
   wherein the second layer of material is a diamond coating.

21. An orthodontic device as claimed in claim 20, and wherein the second layer of material is an amorphous diamond coating.

22. An orthodontic device as claimed in claims 20, and wherein the second layer of material is a polycrystalline diamond coating.

23. An orthodontic device as claimed in claim 20, and wherein the first layer of material is a silica monomer.

* * * * *

UNITED STATES PATENT AND TRADEMARK OFFICE
CERTIFICATE OF CORRECTION

PATENT NO. : 5,575,644
DATED : November 19, 1996
INVENTOR(S) : Lee H. Tuneberg

It is certified that error appears in the above-indentified patent and that said Letters Patent is hereby corrected as shown below:

Title page, item [19] and
Title page, item [75], inventor: delete -- Tuneburg--and insert--Tuneberg--

Signed and Sealed this

Eleventh Day of February, 1997

Attest:

BRUCE LEHMAN

Attesting Officer

Commissioner of Patents and Trademarks